(12) United States Patent
Cao et al.

(10) Patent No.: US 11,633,176 B2
(45) Date of Patent: *Apr. 25, 2023

(54) POSITIONING DEVICES, METHODS, AND SYSTEMS

(71) Applicant: Boston Scientific Scimed, Inc., Maple Grove, MN (US)

(72) Inventors: Hong Cao, Maple Grove, MN (US); Dongming Hou, Plymouth, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 745 days.

This patent is subject to a terminal disclaimer.

(21) Appl. No.: 15/665,057

(22) Filed: Jul. 31, 2017

(65) Prior Publication Data

US 2018/0035986 A1 Feb. 8, 2018

Related U.S. Application Data

(60) Provisional application No. 62/370,455, filed on Aug. 3, 2016.

(51) Int. Cl.
*A61B 10/04* (2006.01)
*A61B 1/018* (2006.01)
(Continued)

(52) U.S. Cl.
CPC .............. *A61B 10/04* (2013.01); *A61B 1/018* (2013.01); *A61B 1/2676* (2013.01); *A61B 8/085* (2013.01);
(Continued)

(58) Field of Classification Search
CPC ..... A61B 10/02; A61B 10/0233; A61B 10/04; A61B 2010/045; A61B 1/012;
(Continued)

(56) References Cited

U.S. PATENT DOCUMENTS 4,750,488 A * 6/1988 Wuchinich ....... A61B 17/22012
604/22
5,398,690 A * 3/1995 Batten .................. A61B 8/0833
600/439
(Continued)

FOREIGN PATENT DOCUMENTS

JP 2001104315 A 4/2001
WO WO-2016025389 A1 * 2/2016 .......... A61B 5/6848

*Primary Examiner* — Ashley K Buran
*Assistant Examiner* — Amy J Shafqat
(74) *Attorney, Agent, or Firm* — Seager, Tufte & Wickhem, LLP

(57) ABSTRACT

Embodiments include devices, methods, and systems for positioning devices. An exemplary method comprises: moving a distal end of a tube into a body, the tube including a lumen and a shaft in the lumen, the shaft having a transducer; sending a first signal to the transducer; passing, with the transducer, in response to the first signal, a wave energy into the body; receiving, with the transducer, a reflected portion of the wave energy; generating, with the transducer, a second signal in response to the reflected portion of the wave energy; determining, with a processor, an indicia of the body in response to the second signal; and identifying, with the indicia, a targeted issue in the body; positioning the distal end of the tube at the targeted tissue in response to the indicia; and removing a portion of the targeted tissue with the distal end of the tube.

18 Claims, 5 Drawing Sheets

(51) Int. Cl.
*A61B 8/12* (2006.01)
*A61B 8/00* (2006.01)
*A61B 8/08* (2006.01)
*A61B 1/267* (2006.01)

(52) U.S. Cl.
CPC ............... *A61B 8/12* (2013.01); *A61B 8/445* (2013.01); *A61B 8/4494* (2013.01); *A61B 2010/045* (2013.01)

(58) Field of Classification Search
CPC ... A61B 1/0125; A61B 1/018; A61B 1/00174; A61B 1/00177; A61B 1/00179; A61B 1/00181; A61B 1/00183; A61B 8/12; A61B 8/445; A61B 8/4455; A61B 8/4461; A61B 8/0833; A61B 8/085; A61B 8/4483; A61B 8/4494; A61B 1/2676
USPC ....... 600/471, 437, 459, 461, 462, 466, 464, 600/467
See application file for complete search history.

(56) References Cited

U.S. PATENT DOCUMENTS

| | | | |
|---|---|---|---|
| 5,487,387 A * | 1/1996 | Trahey | A61B 8/0825 128/915 |
| 6,059,731 A * | 5/2000 | Seward | A61B 8/12 600/459 |
| 6,157,852 A * | 12/2000 | Selmon | A61B 8/12 128/898 |
| 6,306,097 B1 * | 10/2001 | Park | A61B 1/00154 600/466 |
| 6,494,841 B1 * | 12/2002 | Thomas | A61B 8/481 600/447 |
| 6,936,048 B2 | 8/2005 | Hurst | |
| 9,289,185 B2 | 3/2016 | Mung et al. | |
| 2002/0077627 A1 * | 6/2002 | Johnson | A61B 18/1477 606/41 |
| 2004/0252870 A1 * | 12/2004 | Reeves | G06T 7/0012 382/128 |
| 2005/0113693 A1 * | 5/2005 | Smith | A61B 17/12022 600/439 |
| 2006/0253107 A1 * | 11/2006 | Hashimshony | A61B 5/415 606/1 |
| 2008/0114309 A1 | 5/2008 | Zuckerman | |
| 2009/0030312 A1 * | 1/2009 | Hadjicostis | A61B 8/4488 600/439 |
| 2010/0047210 A1 * | 2/2010 | Johnson | A61K 31/70 424/93.7 |
| 2011/0066073 A1 * | 3/2011 | Kuiper | A61B 10/0241 600/562 |
| 2011/0098572 A1 | 4/2011 | Chen et al. | |
| 2014/0171788 A1 * | 6/2014 | Stigall | A61B 17/3403 600/424 |
| 2014/0257102 A1 * | 9/2014 | Hossack | A61B 8/4416 600/440 |
| 2015/0094595 A1 * | 4/2015 | Havel | A61B 8/12 600/467 |
| 2016/0242733 A1 * | 8/2016 | Lenox | A61B 8/0825 |
| 2021/0118130 A1 * | 4/2021 | Zhang | G06T 11/00 |

\* cited by examiner

POSITIONING DEVICES, METHODS, AND SYSTEMS

CROSS-REFERENCE TO RELATED APPLICATIONS

This application claims the benefit of U.S. Provisional Application No. 62/370,455, filed Aug. 3, 2016, the disclosure of which is incorporated herein by reference in its entirety.

TECHNICAL FIELD

Aspects of the present disclosure generally relate to positioning devices, methods, and procedures. In particular, aspects relate to using wave energy to position a medical device in a body.

BACKGROUND

Lung cancer is among the leading causes of cancer deaths worldwide, in part, because most new cases are not presented until later stages of development (e.g., at Stage III or IV). Screening for lung cancer reduces mortality by allowing a greater percentage of new cases to be presented at early stages (e.g., at Stage I or II) where the cancerous tissue can be more easily removed. Many screening procedures comprise, for example, identifying tissues that are suspected to be cancerous (e.g., a lung nodule >8 mm), and performing a lung biopsy on the identified tissue to confirm the presence and/or staging of cancer. In many cases, the lung biopsy is performed by placing a biopsy needle into the lung, and using a series of X-rays to position the biopsy needle at the identified tissue.

There are many problems with known procedures. For example, multiple X-rays may be required to position the biopsy needle, exposing both the patient and the physician to high amounts of radiation. This problem is of particular concern to physicians, and their technicians, who may perform more than one lung biopsy per day, and potentially hundreds per year. Moreover, because each X-ray captures a still image, and multiple X-rays are required to locate the biopsy needle in three dimensions, the physician cannot position the biopsy needle in real-time. Numerous starts and stops are thus required to position the needle, increasing operating times and the potential of damaging non-targeted tissues.

Aspects of the positioning devices, methods, and systems disclosed herein may solve one or more these problems and/or address other missing aspects of the prior art.

SUMMARY

Aspects of the present disclosure relate to positioning devices, methods, and systems. Numerous aspects are now described.

One aspect of this disclosure is a positioning system. An exemplary system may comprise: a tube including a distal end with a tissue penetrating feature and one or more lumens extending through the tube; a shaft positioned in a first lumen of the one or more lumens; a transducer coupled to the shaft, the transducer being configured to generate a wave energy in response to a first signal, receive a reflected portion of the wave energy, and generate a second signal in response to the reflected portion of the wave energy; and one or more processors in communication with the transducer, the one or more processors being configured to generate the first signal, receive the second signal, and output indicia of the body in response to the second signal. In this system, a wave energy impedance of the tube may be similar to a wave energy impedance of the shaft, and the indicia may include a location of a targeted tissue in the body.

According to this aspect, the shaft may be movably positioned in the tube. A distal end of the shaft may include a tissue penetrating feature. The transducer may be mounted on an exterior surface of the shaft, or within an interior of the shaft. In some aspects, the transducer may include, for example, a cylindrical body extending along a central longitudinal axis, a proximal end opposite of a distal end along the central longitudinal axis, an array of side-looking transducers on the cylindrical body, an array of forward-looking transducers on the distal end, and an array of rearward-looking transducers on the proximal end. The array of forward-looking transducers may be movably mounted to the distal end of the cylindrical body. For example, the array of forward-looking transducers may be rotatable about the central longitudinal axis of the cylindrical body, as may any other array described herein. A lumen may extend through the shaft and the transducer. The array of side-looking transducers may be configured to generate a first wave energy, the array of forward-looking transducers may be configured to generate a second wave energy, and the second wave energy may be more focused than the first wave energy. In some aspects, the wave energy may be acoustic energy. For example, the transducer may include at least one piezoelectric ultrasound transducer, and the first and second signals may be electrical signals.

In other aspects, the indicia may include a graphical representation of the body. The one or more processors may be configured to determine, for example, a condition of the targeted tissue from the indicia. In still other aspects, the or more lumens may include a second lumen, and the system may comprise an elongated tool positioned in the second lumen. For example, the elongated tool may be movably positioned in the second lumen and include a working end composed of a shape-memory material that assumes a pre-determined shape when extended distally out of the second lumen.

Another aspect of this disclosure is a positioning method. An exemplary method may comprise: moving a distal end of a tube into a body passageway, the tube including a lumen extending therethrough and a shaft positioned in the lumen, the shaft having a transducer; sending a first signal to the transducer; passing, with the transducer, in response to the first signal, a wave energy into the body passageway through the tube and the shaft; receiving, with the transducer, a reflected portion of the wave energy; generating, with the transducer, a second signal in response to the reflected portion of the wave energy; and determining, with a processor, an indicia of the body passageway in response to the second signal; identifying, with the indicia, a targeted issue in the body passageway. In some aspects, the method may comprise positioning the distal end of the tube at the targeted tissue in response to the indicia; and removing a portion of the targeted tissue with the distal end of the tube.

According to this aspect, the indicia may include a graphical representation of the body, and the method may comprise determining a location of the targeted tissue with the graphical representation. The method may comprise determining a size of the targeted tissue with the indicia. For example, the wave energy may be acoustic energy, and the method may comprise determining, with the processor, a condition of the targeted tissue based on the reflected portion of the acoustic energy. In other aspects, the indicia may include a boundary of the targeted tissue, and the method may comprise determining, with the processor, whether the distal end of the tube has penetrated the boundary.

Yet another aspect of this disclosure is another positioning method. This method may comprise: moving a distal end of a tube in a lung, the tube including a lumen extending therethrough and a shaft positioned in the lumen, the shaft having a transducer mounted therein; sending and receiving, with the transducer, a wave energy through the tube and the shaft; generating, with a processor, using a reflected portion of the wave energy, indicia of the lung; locating, with the indicia, a lung nodule in the lung; guiding, with the indicia, the distal end of the tube into the lung nodule; and removing a portion of the nodule with the distal end of the tube.

According to this aspect, the method may comprise guiding, with the indicia, a distal end of the shaft towards the lung nodule. For example, the indicia may include a graphical representation of the lung (or a portion of the lung), and the method may comprise identifying, with one or more processors, a location of the lung nodule on the graphical representation. The method may comprise determining, from the indicia, a distance between the distal end of the tube and a proximal surface of the lung nodule. The distal end of the shaft may include a tissue penetrating portion, and the method may comprise: moving the tissue penetrating portion of the shaft into the lung nodule; and determining whether the nodule is solid-filled based upon the reflected portion of wave energy. In some aspects, the distal end of the tube may include a tissue penetrating portion, and the method may comprise: determining whether the density of the lung nodule exceeds a pre-determined maximum density; and moving the tissue penetrating portion of the tube into the nodule if the pre-determined maximum density is exceeded. In still other aspects, the shaft may include an echogenic indicator, and the method may comprise determining a location of the echogenic indicator with the indicia. For example, the shaft may include a central longitudinal axis, the echogenic indicator may be offset from the central longitudinal axis, and the method may comprise determining a rotational position of the shaft with the indicia based on the location of the indicator relative to the central longitudinal axis.

Aspects of a positioning device are also disclosed with reference the methods and systems described above. Numerous exemplary devices, methods, and systems are now described in detail below, each including aspects relating to the use of wave energy as a means for positioning a medical device in a body (e.g., in a lung) to identify and confirm the location of a material in the body (e.g., a tumor in the lung), the material having an impedance distinguishable from healthy tissue of the body (e.g., healthy lung tissue).

It may be understood that both the foregoing summary and the following detailed descriptions are exemplary and explanatory only, neither being restrictive of the inventions claimed below.

BRIEF DESCRIPTION OF THE DRAWINGS

The accompanying drawings are incorporated in and constitute a part of this specification. These drawings illustrate aspects of the present disclosure that, together with the written descriptions, serve to explain the principles of this disclosure.

DETAILED DESCRIPTION

Figure 1A:
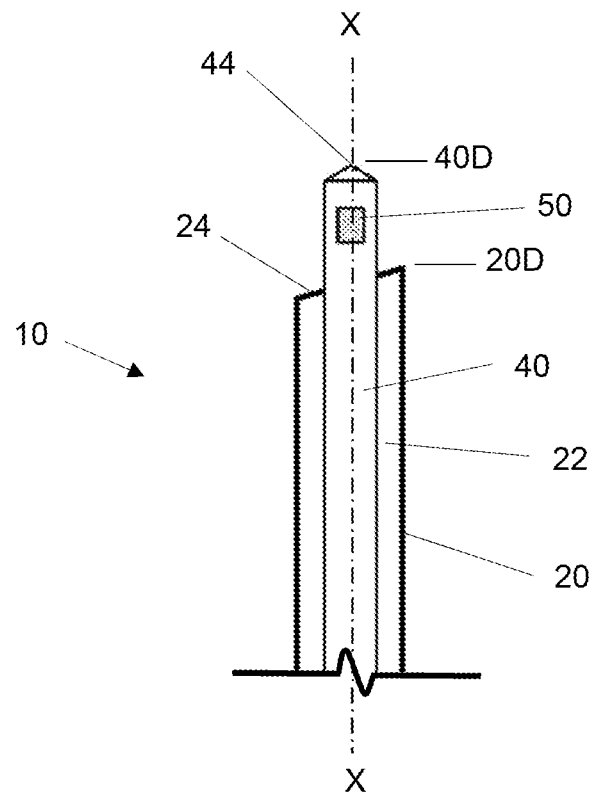
FIG. 1A depicts a side view of an exemplary device.

Aspects of the present disclosure are now described with reference to exemplary positioning devices, methods, and systems. Some aspects are described with reference to a medical procedure (e.g., a lung biopsy), wherein a sensor (e.g., a transducer) is positioned in a body (e.g., in a lung) to identity a targeted tissue in the body (e.g., a solid-filled lung nodule), and guide a needle (e.g., a biopsy needle) toward the targeted tissue. Any reference to a particular procedure, such as a lung biopsy; a particular sensor, such as a transducer; a particular body, such as a lung; or a particular instrument, such as a biopsy needle, is provided for convenience and not intended to limit this disclosure unless claimed. Accordingly, the concepts disclosed herein may be used with any analogous device, method, or system—medical or otherwise.

The directional terms "proximal" and "distal," and their respective initials "P" and "D," are used to describe relative components and features of the present disclosure. Proximal refers to a position closer to the exterior of the body or a user, whereas distal refers to a position closer to the interior of the body or further away from the user. Appending the initials P or D to an element number signifies the element's proximal or distal location. Unless claimed, these directional terms and initials are provided for convenience and not intended to limit the present disclosure to a particular direction or orientation. As used herein, the terms "comprises," "comprising," or like variation, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal."

The relative terms "echogenic" and "anechoic" are used to describe characteristics of certain "materials" in the present disclosure. The term materials may include any organic or non-organic material, including body fluids and tissues. The term echogenic may be attributed to materials with a higher resistance or impedance to a wave energy (also referred to as wave energy impedance), meaning that at least a portion of the wave energy will be reflected off such materials. For example, an echogenic material may produce internal echoes, such as reflections of ultrasound waves. Air and metal, for example, may be considered echogenic materials in some ultrasound applications. The term echogenic may also be used to describe a relative difference between two materials. For example, an internal echo may be produced by a first material (e.g., air) and a second material (e.g., metal) in response to wave energy. If a magnitude of each echo is different, then those materials may be described as echogenic with respect to one another. Conversely, the term anechoic may be attributed to materials with a lower resistance or impedance to wave energy (or low wave energy impedance), meaning that at least a portion of the wave energy will pass through such materials. Healthy lung tissue and certain polymers, for example, may be considered anechoic materials in some ultrasound applications. The term anechoic may also be used to described a relative similarity between two materials. For example, if the magnitude of an echo produced by a first material (e.g., lung tissue) is equal to a magnitude produced by a second material (e.g., a polymer), then those materials may be described as being anechoic with respect to one another. Unless claimed as such, neither of these relative terms, echogenic or anechoic, is intended to be absolute.

The term "indicia" is used in this disclosure to mean any real-time indication of a particular characteristic of a body. One form of indicia is a data model that is generated in response to one or more electrical signals and usable to determine characteristics of the body, such as the location and/or size of a cavity in the body, the location of its boundaries, and the location of a targeted tissue in the cavity. The data model may, for example, be created by an operator or processor, and used by the operator as a real-time guide to position a medical device in the body. Another form of indicia is a two- or three-dimensional graphical representation of the body that is generated in response to the one or more electrical signals, or with the data model. The graphical representation may also be used by the operator as a real-time guide to position a medical device in the body.

One aspect of the present disclosure is an exemplary device 10 configured to generate indicia of a body. As shown in FIG. 1A, device 10 may comprise a tube 20 with a lumen 22 extending therethrough, a shaft 40 in lumen 22, and a transducer 50 in shaft 40. Transducer 50 may generate a wave energy (e.g., acoustic energy, laser energy, vibratory energy, or the like) that is passed into the body through tube 20, shaft 40, and/or a fluid (e.g., saline). According to this disclosure, a reflected portion of the wave energy is returned to transducer 50 from the interior surfaces of the body. Transducer 50 of FIGS. 1A-B generates an electric signal in response to the reflected portion of the wave energy. This electric signal may, in turn, be used to generate indicia of the body.

Tube 20 of FIG. 1A is an elongated element that extends along a central longitudinal axis X-X from a distal end 20D. A lumen 22 extends through tube 20 in a direction parallel to axis X-X, although tube 20 may include any number of lumens 22 extending therethrough. The distal end 20D of tube 20 of FIG. 1A has a penetrating feature 24 configured to penetrate the surfaces of the body. For example, penetrating feature 24 may be an edge of distal end 20D that has been sharpened to remove a portion of tissue from a body when distal end 20D is positioned at the tissue and moved in a linear and/or rotational direction relative thereto. The structure and uses for penetrating feature 24 may include any cutting and/or piercing implementations associated with biopsy needles, including blades, sharpened points, and the like.

Shaft 40 is an elongated element that extends in a direction parallel to axis X-X. In FIG. 1A, shaft 40 is movably positioned in lumen 22. Shaft 40 may be positioned for translational movement (i.e., movement in a proximal-distal direction along axis X-X) and/or rotational movement (i.e., movement about axis X-X). A distal end 40D of shaft 40 of FIG. 1A includes a penetrating feature 44 configured to penetrate the interior surfaces of the body. Penetrating feature 44 of FIG. 1 includes a distal point that is formed on distal end 40D and configured to penetrate tissue when moved out of lumen 22 in a direction parallel to axis X-X. Any aspect of penetrating feature 24 of tube 20 may be used with penetrating feature 44 of shaft 40.

Transducer 50 of FIG. 1A may be mounted on, mounted in, or otherwise coupled to shaft 40 at, for example, a location adjacent distal end 40D. As shown, transducer 50 may include any means for generating and receiving wave energy. For example, transducer 50 may be configured to: generate one or more wave energies in response to a first electrical signal; receive a reflected portion of the wave energies (if present); and generate a second electrical signal in response thereto. Exemplary wave energies may include acoustic energy, laser energy, and the like, such as those energies typically used for ultrasound, lidar, radar, sonar, and the like. The first and second electrical signals may be modified (e.g., pulsed) according to any existing method so as to maximize the capability of a particular wave energy.

In one aspect, the wave energy is acoustic energy, and transducer 50 includes at least one array (e.g., a two- or three-dimensional array) of piezoelectric ultrasound transducers configured to generate an ultrasonic wave (e.g., a pulse or train of pulses) in response to the first electrical signal, and generate the second electrical signal in response to a reflected portion of the ultrasonic wave. A frequency of the ultrasound wave may be selected based upon a desired combination of accuracy and depth. For example, if greater accuracy is desired, then a higher frequency may be used; whereas, if greater depth is required, then a lower frequency may be used. In some aspects, the frequency may be approximately 5 MHz or lower; between approximately 5 and 20 MHz; between approximately 10 and 30 MHz; at least 40 MHz; approximately between 20 and 60 MHz; or approximately 60 MHz or lower. Any suitable intermediate and/or comparable frequency values and/or ranges may be used. In some aspects, a plurality of transducers 50 may used, wherein, responsive to one or more signals, a first portion is configured to optimize accuracy and a second portion is configured to optimize depth.

Figure 1B:
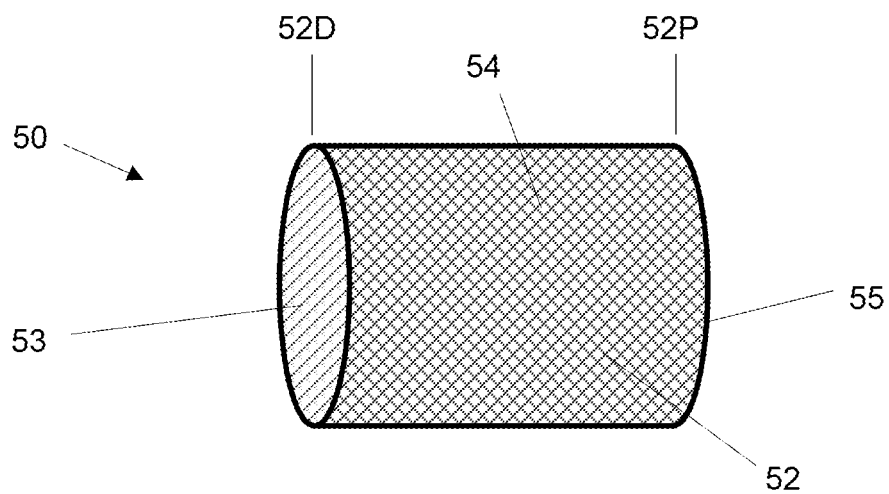
FIG. 1B depicts a side view of an element of the device of FIG. 1A.

An exemplary transducer 50 is illustrated in FIG. 1B as having a cylindrical body 52 with a distal end 52D opposite of a proximal end 52P. As shown, an array of forward transducers 53 is mounted on distal end 52D, while an array of side-looking transducers 54 are mounted on body 52, and an array of rearward-looking transducers 55 is mounted on proximal end 52P. Each array 53, 54, and 55 may include a plurality of transducers that, individually or in combination, generate the wave energy in response to the first electrical signal, and generate the second electrical signal in response to the reflected portion of the wave energy. Each second electrical signal may be used to generate indicia of the body. Arrays 53, 54, and 55 also may be arranged to enhance the indicia. For example, locating forward (53), side (54) and rearward (55) arrays on opposing proximal and distal ends 52P and 52D of body 52 may provide for an accurate, three-dimensional representation of the body no matter the proximal-distal location of transducer 50 relative to tube 20, shaft 40, and/or an interior surface of the body. Although a cylindrical transducer with forward, side, and rearward-looking transducers is shown in FIG. 1B, other suitable shapes and configurations may be used.

Numerous types of indicia may be generated with device 10. For example, the second electrical signal from transducer 50 may be used to generate indicia including geometric data concerning the body, such as the size, shape, and orientation of a cavity in the body. In other aspects, the indicia may further include targeting data concerning the identification and location of a targeted tissue in the body relative to said geometric data. For example, different tissues in the body (e.g., healthy lung or liver tissue versus cancerous lung or liver tissue) may have different wave energy impedances. These differences may be determined from the second electrical signals and used to generate indicia including, in one aspect, a graphical representation of the body that distinguishes between the targeted tissues and other, non-targeted tissues. Using similar comparative methods, the indicia may likewise be used to determine, for example, the relative sizes of each targeted tissue, the density and/or porosity of said tissues, the relative locations of a plurality of said tissues, optimized paths thereto and therebetween, and the like.

Another aspect of the present disclosure is now described with reference to a system 100 including a device 110 that, like device 10, may be used to generate indicia of a body, depicted as a lung 1 in FIG. 2A. In one aspect, system 100 is used to perform a biopsy on a lung nodule 3 in lung 1. System 100 includes a device 110 that is similar to device 10, but within the 100 series of numbers. For example, device 110 of FIG. 2A, similar to device 10 of FIG. 1A, includes a tube 120 with a lumen 122, a shaft 140 in lumen 122, and a transducer 150 mounted on, in, or otherwise coupled to shaft 140. Like reference numbers are used to describe like elements of devices 10 and 110 wherever possible. System 100 further includes a processor 160 in communication with transducer 150.

Figure 2A:
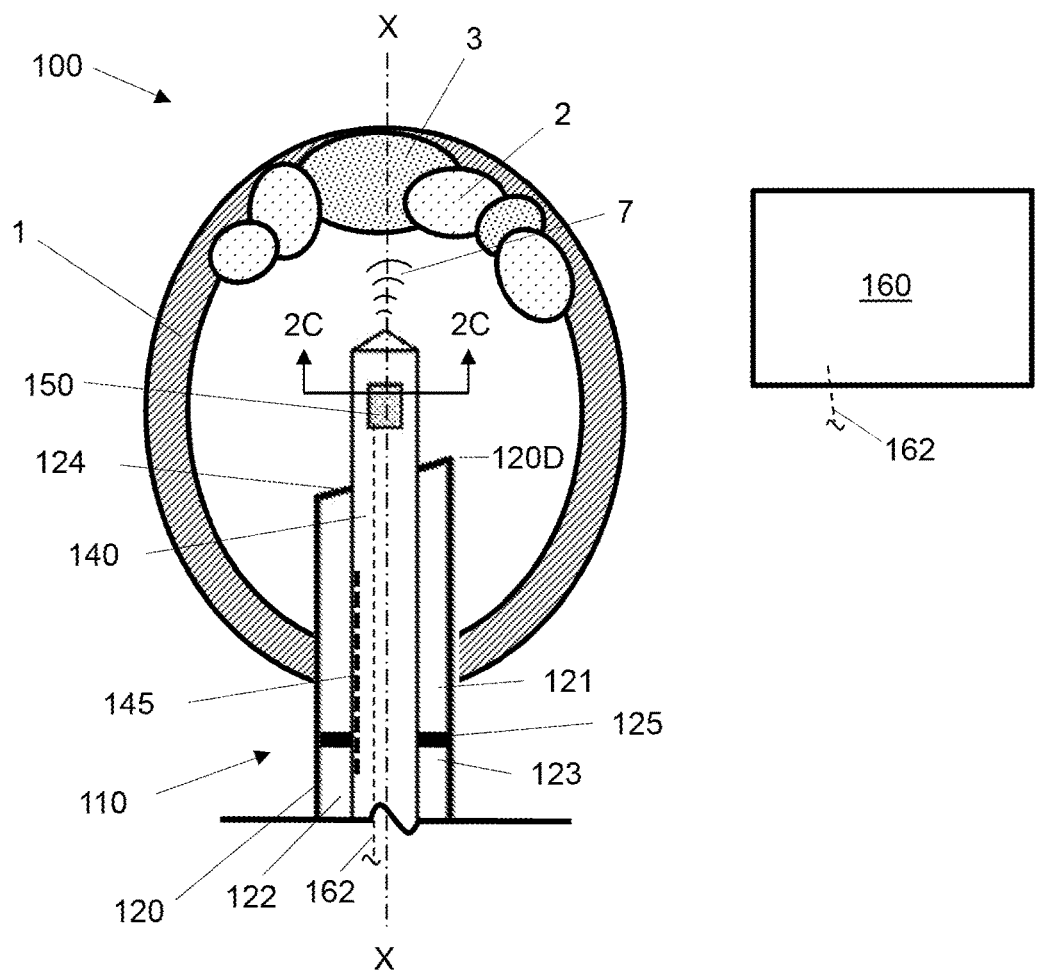
FIG. 2A depicts a side view of an exemplary system.

Tube 120 of FIG. 2A has a distal end 120D, a distal end portion 121, and a proximal end portion 123 arranged linearly along a central longitudinal axis X-X. Distal end 120D has a penetrating feature 124 similar to penetrating feature 24 described above. A lumen 122 extends through end portions 121 and 123 of tube 120 along axis X-X. At least the distal end portion 121 may be composed of an anechoic material having a wave energy impedance similar to that of a body tissue and/or a fluid. According to one aspect of system 100, the anechoic material is a biocompatible and/or polymeric material (e.g., a polyetheretherketone or PEEK) having an acoustic impedance similar to that of the body tissue and/or fluid. These acoustic impedances be approximately equal, or within a range of approximately 10% to 20% of each other. For example, the polymeric material may have an acoustic impedance proximate to that of a healthy tissue (e.g., a lung tissue having an acoustic impedance of about $1.8 \times 10^5$ kg/($M^2$*s)) and/or biocompatible fluid (e.g., a water-based solution having an acoustic impedance of about $1.52 \times 10^6$ kg/($M^2$*s).

Figures 2B, 2C:
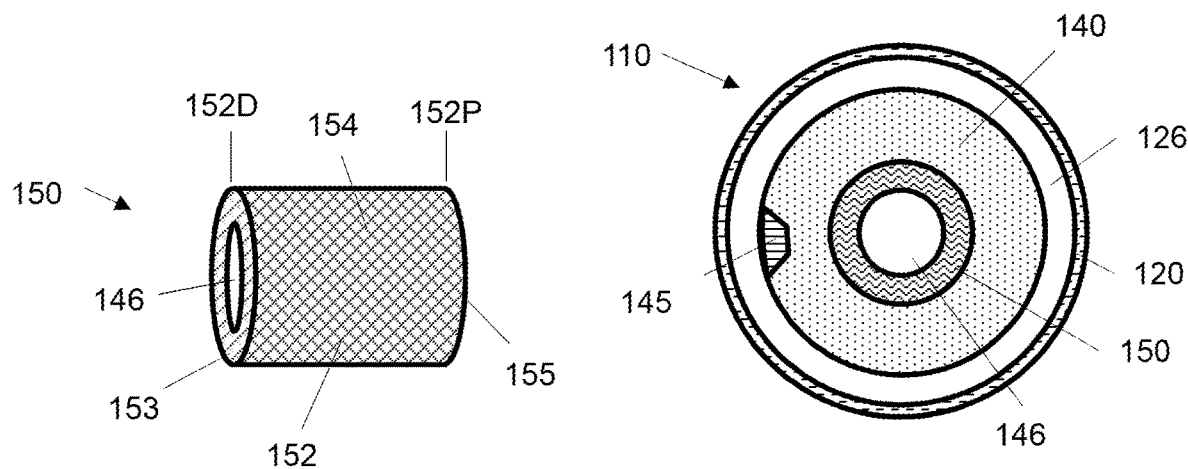
FIG. 2B depicts a side view of an element of the system of FIG. 2A.
FIG. 2C depicts a section view of an exemplary device included in the system of FIG. 2A taken along a section line 2C-2C illustrated in FIG. 2A.

Shaft 140 is movably positioned in lumen 122. A section view of tube 120 and shaft 140 is shown in FIG. 2C. As shown, for example, an exterior diameter of shaft 140 is offset from an interior diameter of lumen 122 to define an annular channel 126. Shaft 140 may be composed of an anechoic material having a wave energy impedance similar to that of the distal end 121 of tube 120 and/or the aforementioned fluid. For example, shaft 140 may be composed of a PEEK tuned to match a body tissue and/or a saline. According to this aspect, the wave energy impedance of tube 120, shaft 140, and the fluid may render any of those elements fully or partially anechoic. For example, the impedance of tube 120 and shaft 140 may be tuned to match the impedance of a body tissue when exposed to a specific type of wave energy. In some aspects, a proximal end portion tube 120 may be composed of the same anechoic material as distal end portion 121 of tube 120.

Tube 120 and shaft 140 may include one or more echogenic markers. For example, as shown in FIG. 2A, a first echogenic marker 125 may separate the distal and proximal end portions 121 and 123 of shaft 120. First marker 125 is depicted as a metallic annulus mounted between end portions 121 and 123. A second echogenic marker 145 may be included on shaft 140. For example, as shown in FIGS. 2B-C, second echogenic marker 145 is depicted as one or more metallic strips mounted on shaft 140. These first and second markers 125 and 145 may, for example, be used individually or in combination to determine the disposition of shaft 140 relative to tube 120. For example, because markers 125 and 145 are made of an echogenic material (e.g., a metal), they may be highlighted on a graphical representation generated from the indicia so that a physician may move (e.g., rotate or steer) shaft 140 by a precise amount (e.g., an incremental distance or angle) relative to tube 120, in real-time, by comparing the relative positions of markers 125 and 145.

An exemplary transducer 150 is depicted in FIGS. 2A-C. As shown in FIG. 2B, transducer 150, like transducer 50, may have a cylindrical body with a distal end 152D opposite of a proximal end 152P. A section view of shaft 140 and transducer 150 is depicted in FIG. 2C. Shaft 140 and transducer 150 of FIG. 2C cooperate to define a shaft lumen 146 extending through shaft 140 in a direction parallel to axis X-X. Similar to above, an array of forward-looking transducers 153 is mounted on distal end 152D, while an array of side-looking transducers 154 is mounted on body 152, and array of rearward-looking transducers 155 is mounted on proximal end 152P. Transducer 150 may be configured to match the capabilities of transducer 50. For example, as above, each array 153, 154, and 155 may be configured to generate a wave energy upon application of a first electrical signal, and generate a second electrical signal upon receiving a reflected portion of the wave energy.

The wave energy impedance of tube 120 and shaft 140 may determine the location of transducer 150. For example, if tube 120 and shaft 140 are made of similar anechoic materials (e.g., PEEK), then the distal end portion 121 of tube 120 may be used to pierce a body tissue, meaning that transducer 150 may be located anywhere on or within shaft 140 and/or tube 120 because a majority of the wave energy will pass through each element. Alternatively, if distal end portion 121 of tube 120 is made of an echogenic material (e.g., stainless steel), then transducer 150 should be located on a portion of shaft 140 that is extendable from tube 120 to expose transducer 150, else a majority of the wave energy will not escape tube 120.

In system 100, the capabilities of transducer 150 may be modified by shaft lumen 146 to permit addition of new arrays, sensors, tools, and the like. In some aspects, at least forward-looking array 153 of FIG. 2B may include, for example, a toroidal transducer configured to generate a wave energy that is more intense and/or focused in a direction parallel to axis X-X, thereby improving the quality of indicia generated with system 100. In some aspects, the array of side-looking transducers 154 may be configured to generate a first wave energy, the array of forward-looking transducers 155 may be configured to generate a second wave energy, and the second wave energy is more focused than the first wave energy, thereby improving the quality of the indicia along axis X-X. Additional arrays may be added to the interior surfaces of lumen 146 for like effect.

A sensor may be provided in lumen 146. For example, a sensor may be placed on an interior surface of lumen 146 to track the location of shaft 140 (or marker 145) relative to tube 120 (or marker 125) as it passes by said sensor along axis X-X. Other elongated elements, such as a guide wire, an optical cable, or an elongated tool, may be delivered to lung 1 through shaft lumen 146.

Figure 3:
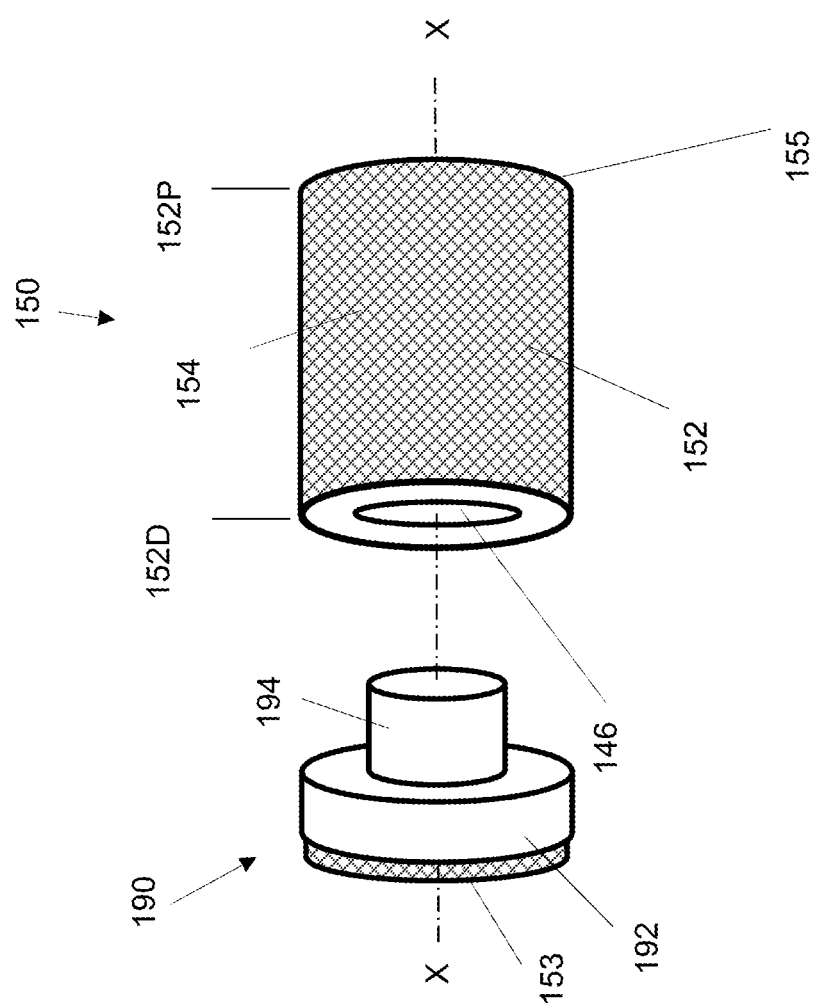
FIG. 3 depicts another exemplary device.

A portion of transducer 150 may be movably mounted in lumen 146. For example, as shown in FIG. 3, forward-looking array 153 of transducer 150 may be a rotational planar transducer that is movably mounted on a distal surface 192 of a platform 190. An actuator 194 may extend proximally from platform 190 for receipt in lumen 146. Actuator 194 may be operable in lumen 146 to move platform 190. For example, actuator 194 may include a motor that is operable with the interior surfaces of lumen 146 to move platform 190, or a portion that extends through lumen 146 for manual operation by application of force to a proximal end of actuator 194. In either instance, forward-looking array 153 is rotatable about axis X-X to modify the indicia. Similar modifications may be made to side-looking array 154 and/or rearward-looking array 155 without departing from this disclosure. For example, each array 153, 154, and 155 may be independently rotatable about axis X-X.

Processor 160 is in communication with transducer 150 and may include one or more processors that are local (e.g., an element of device 10) and/or remote (e.g., an internet connected server) thereto. Any wired or wireless means may be used to facilitate communication between processor 160 and transducer 150. In FIG. 2A, for example, a set of conductors 162 extend between transducer 150 and processor 160. Conductors 162 may include, for example, at least one conductor 162 extending between processor 160 and each array 153, 154, and 155 to deliver the first electrical signal from processor 160 to array 153-155; and deliver the second electrical signal from arrays 153-155 to processor 160.

Processor 160 outputs indicia of lung 1 in response to the second electrical signals. For example, as illustrated in FIG. 2A, the wave energy may be an acoustic energy 7, and lung 1 may include a plurality of air-filled lung nodules 2 and a plurality of solid-filled lung nodules 3. Because the acoustic impedance of each air-filled nodule 2 may be lower than the acoustic impedance of each solid-filled nodule 3, the magnitude of acoustic energy reflected from an air-filled nodule 2 may be less than the magnitude of acoustic energy reflected from a solid-filled nodule 3. These magnitude difference are reflected in the second electrical signals, which may then be analyzed by processor 160 to output the indicia. To continue the previous example, processor 160 may use the magnitude of each second electrical signal to generate a graphical representation of lung 1, and the respective differences between each magnitude to locate one or more solid-filled lung nodules 3 on the graphical representation. An operator may, thus, use the representation as a real-time guide to position distal end 120D of device 110 at one of the solid-filled nodules 3.

Using other comparative methods, processor 160 may likewise be used to determine, for example, the size of a particular solid-filled nodule 3, the location of a plurality of nodules 3 in lung 1, a condition (e.g., the density) of a particular nodule 3, and the like. Still other capabilities may be realized with system 100. For example, because each of tube 120, shaft 140, and the fluid have as similar wave energy impedance, transducer 150 may be "always-on" because the indicia output by processor 160 is not affected by the position of shaft 140 relative to tube 120. In this regard, there is no need to position the distal end 140D of shaft 140 at a point distal of the distal end 120D of tube 120, as shown in FIG. 2A. As a further example, because of shaft lumen 146, processor 160 may be in communication with another element extending through lumen 146, such as a laser source coupled to an optical fiber that extends through lumen 146 to direct a wave energy (i.e., laser energy) towards one of the solid-filled nodules 3.

Figure 4A:
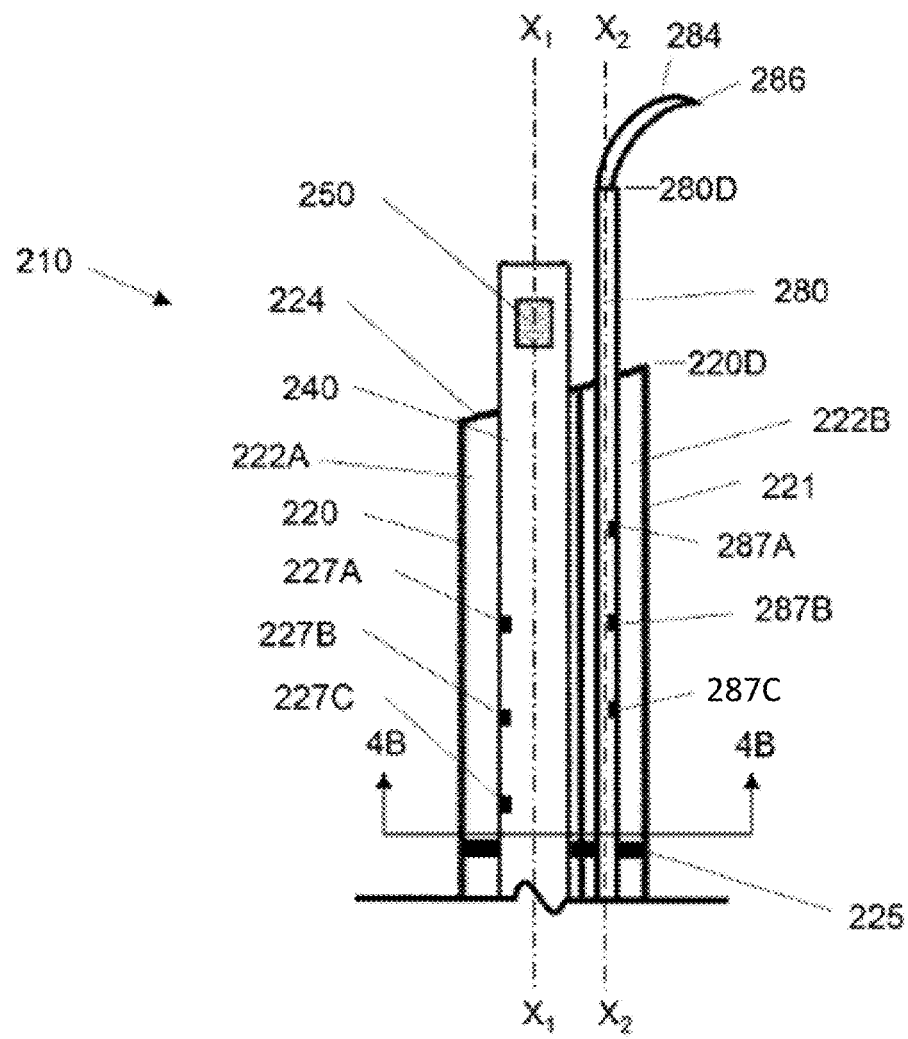
FIG. 4A depicts another exemplary device.

Still other aspects of the present disclosure are described with reference to a device 210. As shown in FIG. 4A, device 210, like devices 10 (FIG. 1A) and 110 (FIG. 2A), may be used to generate indicia of a body. Like element numbers are used to describe like components of device 210 wherever possible, but within the 200 series of numbers. For example, device 210 of FIG. 4A, similar to device 10 of FIG. 1A, includes a tube 220 with a first lumen 222A, a shaft 240 in first lumen 222A, and a transducer 250 in or on shaft 240. In contrast to above, tube 220 includes a second lumen 222B, and an elongated tool 280 in second lumen 222B.

Figure 4B:
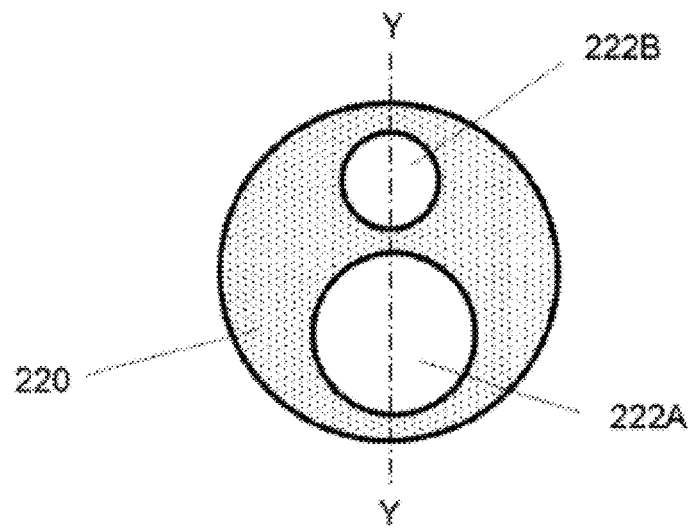
FIG. 4B depicts a side view of an element of the system of FIG. 4A.
Figure 5:
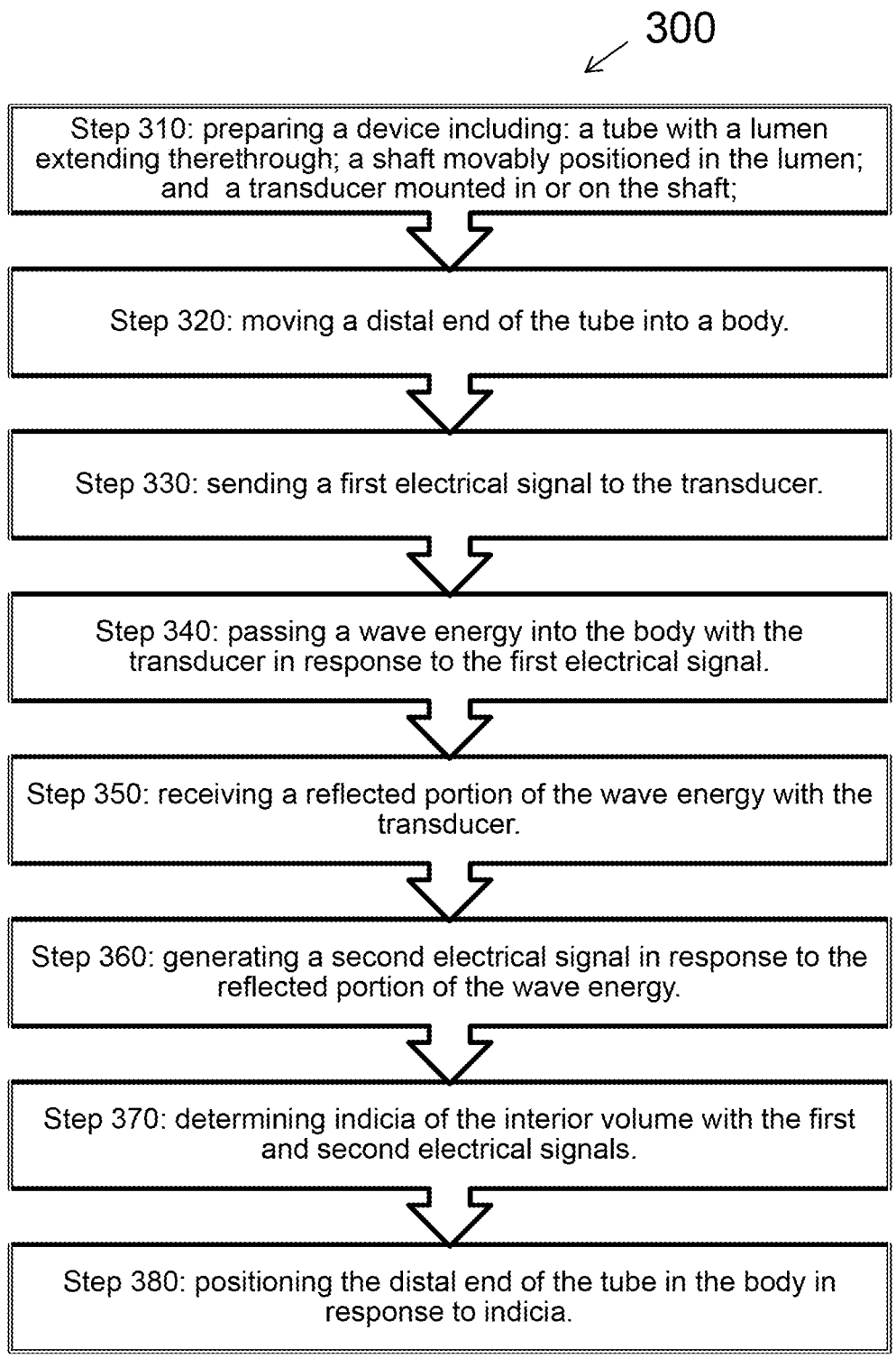
FIG. 5 depicts an exemplary method.

For tube 220, first lumen 222A extends through tube 220 along first axis $X_1$-$X_1$, while second lumen 222B extends through tube 220 along a second longitudinal axis $X_2$-$X_2$ that is parallel to first longitudinal axis $X_1$-$X_1$. A section view of tube 220 is provided in FIG. 4B. As shown, lumen 222A and axis $X_1$-$X_1$ are offset from lumen 222B and axis $X_2$-$X_2$ along a lateral axis Y-Y. Shaft 240 is movable in first lumen 222A relative to axis $X_1$-$X_1$, like shafts 40 and 140 described above. Transducer 250 is mounted in, on, or otherwise coupled to shaft 240 of FIG. 4A and configured to generate wave energy and responsive electrical signals like those described for transducers 50 and 150. At least a distal end portion 221 of tube 220 and/or shaft 240 may be composed of an anechoic material with a wave energy impedance similar to a fluid, such as saline. As shown in FIG. 4A, the distal end 220D of tube 220 has a penetrating feature 224.

Elongated tool 280 is movable in second lumen 222B relative to axis $X_2$-$X_2$ in a translational and rotational manner. For example, the distal end 220D of tube 220 may be placed adjacent tissue (e.g., tissue 3 of FIG. 2A) so that a distal end 280D of tool 280 may be moved distally to engage the tissue. Tool 280 of FIG. 4A has a working end 284 configured to perform a procedure on the tissue. In one aspect, working end 284 is composed of a shape-memory metal that forms a pre-determined shape when end 284 is extended distally from, and thus unrestrained by, lumen 222B. The pre-determined shape of end 284 illustrated in FIG. 4A may position a tip 286 of working end 284 adjacent a tissue along an axis transverse to axis $X_1$-$X_1$ and/or $X_2$-$X_2$.

All or at least portions of elongated tool 280 may have a wave energy impedance similar to that of tube 220, shaft 240, and/or the fluid, allowing the wave energy to pass through each of those elements. If composed of a metal, then working end 284 may have a different wave energy impedance so that the position of tip 286 may be determined from the indicia. For example, in a graphical representation generated from the indicia, using the wave energy, working end 284 and tip 286 may be distinguishable from the body, a targeted tissue in the body, and the remainder of device 210, each of which may have a wave energy impedance different from that of tip 286.

Various echogenic markers may be provided on tube 220, shaft 240, and/or tool 280 so that the relative locations of these elements may be determined from the indicia. FIG. 4A, for example, shows a tube 220 with a first echogenic marker 225 separating the distal end portion 221 of tube 220 from the remainder of tube 220. In one aspect, first marker 225 is a metal annulus. Shaft 240 of FIG. 4A includes a plurality of second echogenic markers 227A-C extending along a length thereof. Either of markers 227A-C and 287A-C may be a plurality of metal strips spaced apart longitudinally on shaft 240 or tool 280 at regular intervals. Accordingly, the indicia may be used to determine a distance between distal end 220D of tube 220 and transducer 250 by comparing the distance between marker 225 and one of markers 227A-C. An operator may, for example, use the indicia to determine an extension depth for shaft 240 by comparing, in real-time, the distance between first marker 225 and one or more of the second markers 227A-C.

The operator may also use the indicia to determine a distance between distal end 220D of tube 220 and portions of tool 280. As shown in FIG. 4A, for example, tool 280 may include a plurality of third echogenic markers 287A-C extending along a length thereof. An operator may, thus, use the indicia to determine an extension depth for tool 280 by comparing, in real-time, the distance between first marker 225 and one or more of third markers 287A-C. In some aspects, the distance between marker 225 and one of markers 287A-C of FIG. 4A may be used to determine whether working end 284 has been extended from second lumen 222B and/or assumed its pre-determined shape. For example, a first distance between the distal-most marker 287A and the intermediate marker 287B may be used to determine whether tip 286 has been extended out of second lumen 222B, while a second distance between intermediate marker 287B and the proximal-most marker 287C may be used to determine whether working end 284 has assumed its pre-determined shape. In some aspects, the pre-determined shape of working end 284 may be configured so that each (e.g., incremental) movement of tool 280 along axis $X_2$-$X_2$ moves tip 286 by a corresponding (e.g., incremental) amount in a direction transverse to axis $X_2$-$X_2$.

Other aspects of the present disclosure include exemplary methods of using devices 10, 110, and 210. An exemplary method 300 is shown in FIG. 4 and now described with reference to device 10 of FIGS. 1A-B. The illustrated method comprises: preparing device 10, which includes tube 20, shaft 40, and transducer 50 (310); moving distal end 20D of tube 20 into an body (320); sending a first electrical signal to transducer 50 (330); passing a wave energy into the body with transducer 50 in response to the first electrical signal (340); receiving a reflected portion of the wave energy with transducer 50 (350); generating a second electrical signal in response to the reflected portion of the wave energy (360); and determining indicia of the body with the first and second electrical signals (370). Method 300 may optionally include positioning, for example, the distal end 20D of the tube 20 in the body in response to the indicia (380).

Preparing device 10 (310) may include any methods necessary to generate the indicia, such as sterilization, providing power, enabling communications, and the like. Moving distal end 20D (320) may likewise include any methods necessary to access the body, including invasive and non-invasive surgical methods, and/or methods of imaging guidance. Sending the first electrical signal to transducer 50 (330) may be performed by a processor, such as processor 160 of FIG. 2A. A wave energy may then be generated by transducer 50 and passed into the body in response to the first electrical signal (340). For example, as described above, transducer 50 may be a piezoelectric actuator that generates an acoustic wave energy by oscillating in response to the first electrical signal. A reflected portion of the wave energy may be returned to transducer 50 from the interior surfaces of the body. Thus, method 300 at 350 further includes receiving a reflected portion of wave energy with transducer 50.

The wave energy may be sent and received through portions of tube 20 and shaft 40. To enhance the indicia, each of tube 20 and shaft 40 may have a similar wave energy impedance so that the wave energy may be passed through tube 20 and shaft 40 without distortion. For example, moving distal end 20D of tube 20 into a body (320) may further comprise moving shaft 40 relative to tube 20 until distal end 20D of tube 20 is distal of distal end 40D of shaft 40. Because tube 20 and shaft 40 share a common wave energy impedance, the quality of any indicia generated from the second electrical signal may be similar no matter the position of distal ends 20D and 40D.

Generating a second electrical signal in response to the reflected portion of the wave energy (360) may be performed by transducer 50. If transducer 50 includes arrays 53, 54, and 55, as described above, and each array 53, 54, and 55 generates a plurality of second electrical signals, then generating the second electrical signal (360) may further comprise combining the plurality of second signals. Determining an indicia of the body with the first and second signals (370) may be performed by a processor that, as described above, analyzes the first and second signals, performs various calculations therewith, and outputs the indicia. These determinations (370) may further include determining a magnitude and/or timing of each second electrical signal, comparing the magnitudes and/or timing of each second signal, and identifying a targeted tissue in the body based upon such comparisons. Similar comparative methods be used to determine, for example, the size of the targeted tissue, the location of a plurality of such tissues, a condition of said tissues (e.g., density or porosity), and the like. Aspects of the wave energy may be varied to support these determinations. For example, method 300 may further include identifying the boundaries of the body with a first wave energy generated by transducer 50, and identifying a targeted tissue in the body with a second wave energy generated by transducer 50.

Although not required, method 300 of FIG. 4 may further include positioning distal end 20D of the tube 20 adjacent a targeted tissue in the body (e.g., healthy lung tissue and/or a lung tumor) in response to the indicia (380). Distal end 40D of shaft 40 may be similarly positioned. In some aspects, distal end 20D is positioned by a machine in response to indicia including a data model; while in other aspects, distal end 20D is positioned by a human in response to indicia including a graphical representation of the body. Distal ends 20D and/or 40D may be positioned at the targeted tissue in this manner. Method 300 may further comprise: confirming that distal end 20D, for example, is positioned at the targeted tissue, and performing a procedure on the targeted tissue. An exemplary procedure may, for example, including removing shaft 40 from lumen 22, and performing an aspiration biopsy on the targeted tissue.

Aspects of method 300 may be modified for use with system 100. For example, each of tube 120 and shaft 140 may have a similar wave energy impedance to the fluid so that the wave energy may be passed through tube 120, shaft 140, and/or the fluid without distortion. In other aspects of method 300, the first electrical signal may be sent by processor 160 at 330, the second electrical signal may be received at processor 160 at 360, and processor 160 may be used to determine the indicia at 370. Because of processor 160, any number of additional determination steps may be included in method 300, including those described herein. Echogenic markers 125 and 145 of system 100 (FIGS. 2A and C) may also be used with method 300. For example, method 300 at 370 and 380 may comprise determining indicia including a distance between distal end 120D of tube 120 and a solid-filled lung nodule 3, and moving first echogenic marker 125 on tube 120 relative to second echogenic marker 145 on shaft 140 by an amount equal to said distance. In other aspects, method 300 may further include removing shaft 140 from tube 120, and either removing fluid from lung 1, or performing an aspiration biopsy on solid-filled lung nodule 3.

Still other aspects of method 300 may be modified for use with device 220. For example, positioning the distal end 220D of tube 220 (380) may further include positioning the distal end 280D of tool 280 at the targeted tissue. The indicia determined at 370 of method 300 may be used to guide working end 284 of tool 280. For example, method 300 may further comprise determining a distance between tip 286 and a targeted tissue, and moving tube 220 and/or tool 280 to ensure that tip 286 will be moved toward the targeted tissue when working end 284 forms its pre-determined shape. Additional echogenic markers may be placed on tube 220 and/or tool 280 to facilitate such movements.

The various aspects of method 300 may be performed in any order. Moreover, in some aspects, method 300 may comprise less than all of the described aspects without departing from this disclosure. For example, the aspects of method 300 at 310 and/or 380 of FIG. 4 may be omitted. Method 300 also may be modified to accommodate the various capabilities and structures of devices 10, 110, and/or 210 described herein, each possible variation being part of this disclosure.

While principles of the present disclosure are disclosed herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects disclosed herein. Accordingly, the present disclosure is not to be considered as limited by the foregoing description.

The invention claimed is:

1. A system for obtaining a tissue biopsy from a body, the system comprising:
   a tube including a distal end with a first tissue penetrating feature and one or more lumens extending through the tube;
   a shaft movably positioned in a first lumen of the one or more lumens extending through the tube, wherein a distal end of the shaft includes a second tissue penetrating feature configured to penetrate tissue while extended out of the first lumen;
   a transducer coupled to the shaft, the transducer being configured to generate a wave energy in response to a first transmission signal, receive a plurality of reflected portions of the wave energy, wherein each of the plurality of reflected portions of the wave energy have a corresponding magnitude value, generate a plurality of second signals including a first signal based on the corresponding magnitude value of a first reflected portion of the plurality of reflected portions of the wave energy, receive a second reflected portion of the plurality of portions of the wave energy, and generate the plurality of second signals including a second signal based on the corresponding magnitude value of the second reflected portion of the wave energy; and
   one or more processors in communication with the transducer, the one or more processors being configured to:
      generate the first transmission signal,
      receive the plurality of second signals including the first signal and the second signal, wherein the first signal includes the corresponding magnitude value of the first reflected portion of the plurality of reflected portions of the wave energy and the second signal includes the corresponding magnitude value of the second reflected portion of the plurality of reflected portions of the wave energy,
      analyze the corresponding magnitude value of the first reflected portion of the plurality of reflected portions of the wave energy with the corresponding magnitude value of the second reflected portion of the plurality of reflected portions of the wave energy,
      determine the respective difference of each magnitude value to identify a first lung nodule corresponding to the first signal of plurality of second signals and to identify a second lung nodule corresponding to the second signal of the plurality of second signals, and
      output indicia of the first lung nodule as targeted tissue and the second lung nodule as non-targeted tissue.

2. The system of claim 1, wherein the transducer is located within an interior of the shaft.

3. The system of claim 2, wherein the transducer includes an array of side-looking transducers, an array of forward-looking transducers, and an array of rearward-looking transducers.

4. The system of claim 3, wherein the array of forward-looking transducers is movable relative to the shaft.

5. The system of claim 1, wherein the transducer includes at least one piezoelectric ultrasound transducer, and the first and second signals are electrical signals.

6. The system of claim 1, wherein the indicia includes a graphical representation of the body.

7. The system of claim 1, wherein the transducer includes one or more of an array of side-looking transducers, an array of forward-looking transducers, and an array of rearward-looking transducers.

8. The system of claim 1, wherein a processor of the one or more processors is configured to determine a condition of the targeted tissue based on the reflected portion of the wave energy.

9. The system of claim 1, wherein the indicia includes a graphical representation of the first lung nodule as the targeted tissue and the second lung nodule as the non-targeted tissue.

10. An apparatus for obtaining a tissue biopsy from a body, the apparatus comprising:
   a tube comprising one or more lumens extending through the tube;
   a shaft positioned in a first lumen of the one or more lumens extending through the tube, wherein a distal end of the shaft includes a tissue penetrating feature configured to penetrate tissue while extended out of the first lumen; and
   a transducer coupled to the shaft, the transducer being configured to:
      generate a first wave energy in response to a first transmission signal,
      receive a reflected portion of the first wave energy, wherein the reflected portion of the first wave energy has a first magnitude value,
      generate a first signal of a plurality of second signals based on the first magnitude value,
      generate a second wave energy in response to a second transmission signal,
      receive a reflected portion of the second wave energy, wherein the reflected portion of the second wave energy has a second magnitude value, and
      generate a second signal of the plurality of second signals based on the second magnitude value,
   wherein one or more processors in communication with the transducer are configured to:
      generate the first transmission signal, receive the first signal of the plurality of second signals, identify a first nodule based on the first signal of the plurality of second signals, generate the second transmission signal, receive the second signal of the plurality of second signals, identify a second nodule based on the second signal of the plurality of second signals, compare a magnitude of the first signal of the plurality of second signals to a magnitude of the second signal of the plurality of second signals to identify the first nodule as a targeted tissue and the second nodule as a non-targeted tissue, and output indicia comprising a graphical representation that identifies the first nodule as the targeted tissue and the second nodule as the non-targeted tissue.

11. The apparatus of claim 10, wherein the transducer is located within an interior of the shaft.

12. The apparatus of claim 11, wherein the transducer includes an array of side-looking transducers, an array of forward-looking transducers, and an array of rearward-looking transducers.

13. The apparatus of claim 12, wherein the array of forward-looking transducers is movable relative to the shaft.

14. The apparatus of claim 10, wherein the transducer includes at least one piezoelectric ultrasound transducer, and the first and second signals are electrical signals.

15. The apparatus of claim 10, wherein the wave energy is acoustic energy.

16. The apparatus of claim 10, wherein the transducer includes an array of forward-looking transducers.

17. The apparatus of claim 16, wherein the array of forward-looking transducers is movable relative to the shaft.

18. The apparatus of claim 16, wherein the transducer includes the array of forward-looking transducers and one or more of an array of side looking transducers and an array of rearward-looking transducers.

* * * * *